(12) United States Patent
Kemp et al.

(10) Patent No.: US 9,457,149 B2
(45) Date of Patent: Oct. 4, 2016

(54) BACK-END DEVICE FOR AN AUTO-INJECTOR AND AUTO-INJECTOR

(75) Inventors: Thomas Mark Kemp, Hertfordshire (GB); Douglas Jennings, Herts (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 679 days.

(21) Appl. No.: 13/996,420
(22) PCT Filed: Dec. 21, 2011
(86) PCT No.: PCT/EP2011/073509
§ 371 (c)(1),
(2), (4) Date: Jun. 20, 2013
(87) PCT Pub. No.: WO2012/085028
PCT Pub. Date: Jun. 28, 2012

(65) Prior Publication Data
US 2013/0267897 A1 Oct. 10, 2013

(30) Foreign Application Priority Data
Dec. 21, 2010 (EP) ..................... 10196074

(51) Int. Cl.
*A61M 5/20* (2006.01)
*A61M 5/32* (2006.01)
(Continued)

(52) U.S. Cl.
CPC ............ *A61M 5/2033* (2013.01); *A61M 5/20* (2013.01); *A61M 5/326* (2013.01); *A61M 5/24* (2013.01);
(Continued)

(58) Field of Classification Search
CPC ............ A61M 5/326; A61M 5/3269; A61M 5/3272; A61M 2005/3261; A61M 2005/3167; A61M 2005/3263; A61M 2005/3264; A61M 2005/206; A61M 2005/208
See application file for complete search history.

(56) References Cited

U.S. PATENT DOCUMENTS 6,270,479 B1 * 8/2001 Bergens .............. A61M 5/2033
604/156

7,988,675 B2 * 8/2011 Gillespie, III ...... A61M 5/2033
604/181

(Continued)

FOREIGN PATENT DOCUMENTS

FR 2905273 A1 3/2008
JP 2005-525879 9/2005
(Continued)

*Primary Examiner* — Andrew Gilbert
(74) *Attorney, Agent, or Firm* — Fish & Richardson P.C.

(57) ABSTRACT

According to the invention, a back-end device of an auto-injector adapted to be attached to a packaged syringe comprises
a plunger arranged to abut against a stopper of the packaged syringe to translate an injection needle of the packaged syringe in a proximal direction and to expel a dose of a medicament contained in the packaged syringe through the injection needle,
a drive means capable of, upon release, driving the plunger in the proximal direction towards a proximal position,
a rotary sleeve with a cam surface adapted to be engaged by a plunger follower formed to the plunger,
a torsion spring arranged to exert a torque upon the rotary sleeve and
a release element capable of, upon manual actuation, releasing the engagement of the plunger follower with the cam surface. The plunger follower is arranged to engage the cam surface to prevent the rotary sleeve from rotating with respect to the chassis in an initial state. Furthermore, in the initial state the plunger follower is arranged to engage the cam surface to prevent an axial translation of the plunger in the proximal direction. Upon release of the engagement of the plunger follower with the cam surface, the rotary sleeve is arranged to rotate within the chassis. The cam surface re-engages the plunger follower after a time delay determined by a rotation speed of the rotary sleeve. The time delay is set so as to allow the cam surface to re-engage the plunger follower after the plunger reaches the proximal position. The cam surface is arranged to withdraw the plunger from the proximal position in a distal direction by continued rotation of the rotary sleeve.

20 Claims, 3 Drawing Sheets

(51) Int. Cl.
*A61M 5/24* (2006.01)
*A61M 5/46* (2006.01)

(52) U.S. Cl.
CPC .......... *A61M 5/46* (2013.01); *A61M 2005/206* (2013.01); *A61M 2005/208* (2013.01); *A61M 2005/2086* (2013.01)

(56) References Cited

U.S. PATENT DOCUMENTS

| | | | | |
|---|---|---|---|---|
| 8,043,262 | B2* | 10/2011 | Streit | A61M 5/2033 604/137 |
| 8,227,016 | B2* | 7/2012 | Thornton | A61L 31/10 427/2.1 |
| 8,568,359 | B2* | 10/2013 | Carrel | A61M 5/2033 604/131 |
| 8,734,402 | B2* | 5/2014 | Sharp | A61M 5/002 604/198 |
| 9,011,387 | B2* | 4/2015 | Ekman | A61M 5/2033 604/197 |
| 2002/0095120 | A1 | 7/2002 | Larsen et al. | |
| 2005/0222539 | A1* | 10/2005 | Gonzales | A61M 5/2033 604/207 |
| 2005/0273055 | A1* | 12/2005 | Harrison | A61M 5/326 604/136 |
| 2006/0287630 | A1 | 12/2006 | Hommann | |
| 2007/0135767 | A1* | 6/2007 | Gillespie | A61M 5/2033 604/135 |
| 2008/0262438 | A1* | 10/2008 | Bollenbach | A61M 5/2033 604/207 |
| 2010/0049125 | A1* | 2/2010 | James | A61M 5/2033 604/110 |
| 2010/0280460 | A1* | 11/2010 | Markussen | A61M 5/2033 604/195 |

FOREIGN PATENT DOCUMENTS

| | | |
|---|---|---|
| JP | 2006-510465 | 3/2006 |
| JP | 2006-334409 | 12/2006 |
| JP | 2008-500856 | 1/2008 |
| JP | 2008-521482 | 6/2008 |
| WO | WO 03/097133 | 11/2003 |
| WO | WO 2005/115516 | 12/2005 |
| WO | 2009037141 A1 | 3/2009 |
| WO | 2009081133 A1 | 7/2009 |
| WO | WO 2009/141219 | 11/2009 |
| WO | WO 2009/153542 | 12/2009 |

\* cited by examiner

BACK-END DEVICE FOR AN AUTO-INJECTOR AND AUTO-INJECTOR

CROSS REFERENCE TO RELATED APPLICATIONS

The present application is a U.S. National Phase Application pursuant to 35 U.S.C. §371 of International Application No. PCT/EP2011/073509 filed Dec. 21, 2011, which claims priority to European Patent Application No. 10196074.8 filed Dec. 21, 2010. The entire disclosure contents of these applications are herewith incorporated by reference into the present application.

FIELD OF INVENTION

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved back-end device for an auto-injector.

It is a further object of the present invention to provide an improved auto-injector.

The object is achieved by a back-end device for an auto-injector according to claim 1 and an auto-injector according to claim 8.

Preferred embodiments of the invention are given in the dependent claims.

In the context of this specification, the terms distal and proximal are defined from the point of view of a person receiving an injection. Consequently, a proximal direction refers to a direction pointing towards the body of a patient receiving the injection and a proximal end defines an end of an element that is directed towards the body of the patient. Respectively, the distal end of an element or the distal direction is directed away from the body of the patient receiving the injection and opposite to the proximal end or proximal direction.

According to the invention, a back-end device of an auto-injector adapted to be attached to a packaged syringe comprises a plunger arranged to abut against a stopper of the packaged syringe to translate an injection needle of the packaged syringe in a proximal direction and to expel a dose of a medicament contained in the packaged syringe through the injection needle, a drive means capable of, upon release, driving the plunger in the proximal direction towards a proximal position, a rotary sleeve with a cam surface adapted to be engaged by a plunger follower formed to the plunger, a torsion spring arranged to exert a torque upon the rotary sleeve and a release element capable of, upon manual actuation, releasing the engagement of the plunger follower with the cam surface. The plunger follower is arranged to engage the cam surface to prevent the rotary sleeve from rotating with respect to the chassis in an initial state. Furthermore, in the initial state the plunger follower is arranged to engage the cam surface to prevent an axial translation of the plunger in the proximal direction. Upon release of the engagement of the plunger follower with the cam surface, the rotary sleeve is arranged to rotate within the chassis. The cam surface re-engages the plunger follower after a time delay determined by a rotation speed of the rotary sleeve. The time delay is set so as to allow the cam surface to re-engage the plunger follower after the plunger reaches the proximal position. The cam surface is arranged to withdraw the plunger from the proximal position in a distal direction by continued rotation of the rotary sleeve.

The back-end device of the auto-injector provides a mechanism for carrying out an injection cycle that may be divided into a needle insertion phase, an injection phase and a needle withdrawal phase. During the needle insertion phase, the injection needle is inserted into the skin of a patient receiving an injection. Subsequently, the dose of the medicament is expelled through the injection needle in the injection phase of the injection cycle. After the dose of medicament has been completely expelled, the injection needle is retracted from the skin of the patient in the needle withdrawal phase. The injection cycle is controlled by an axial translation of the plunger of the back-end device. The mechanism of the back-end device purely relies on mechanical energy sources like, in particular, compression and torsion springs. After an injection cycle has been performed, the back-end device is reset to an initial configuration allowing for a reuse of the back-end device. The back-end device is designed to be attached to the packaged syringe that may, in particular, be arranged as a single-use device. Separation of the auto-injector in a re-usable back-end device and a disposable packaged syringe provides an economic and ecologic advantageous solution, as it allows for the reduction of production costs and minimizes waste, as the back-end device may be used to carry out a plurality of injection cycles.

The injection cycle is commenced by the release of the plunger that is initially axially fixed by the engagement of the cam surface on the rotary sleeve with the plunger follower. The rotary sleeve is arranged to rotate with respect to the plunger and to the chassis throughout the whole injection cycle. The rotary sleeve is adapted to re-engage the plunger follower after the pre-determined time delay has passed and, in particular, the injection phase of the injection cycle has passed. At the end of the injection phase, the plunger reaches the proximal position. The time delay is determined by the rotation speed of the rotary sleeve driven by the torsion spring. In particular, the modulus of resilience of the drive means driving the plunger and the torsion spring are adapted to each other to achieve that the plunger reaches the proximal position and the dose of the medicament is completely expelled before the cam surface re-engages the plunger follower to axially translate the plunger from the proximal position in the distal direction. Retraction of the plunger from the proximal position allows for a withdrawal of the injection needle during the needle withdrawal phase. Thus, the injection needle is withdrawn after the set time delay that is sufficiently long to allow for a complete delivery of the dose of the medicament.

The rotation of the rotary sleeve determines the time span required to finish one injection cycle and ensures that the injection cycle always takes the same time when the auto-injector is used for several injections. The repeatability of the time span required for the injection cycle reduces the injury risk while injecting the dose of the medicament. If the time span is highly variable between different injections then the user may be confused and make errors in delivering the injection.

According to a possible embodiment of the invention, a rotary damper is arranged to exert a velocity dependant torque upon the rotary sleeve. The maximal rotation speed of the rotary sleeve is restricted to a suitable constant value. This in turn sets the time delay to a suitable value, so that the packaged syringe is completely emptied before the injection needle is withdrawn from the skin of the patient.

Preferably, the rotary damper comprises a first cog wheel that engages a second cog wheel of the rotary sleeve to ensure a reliable coupling between the rotary sleeve and the rotary damper.

According to another possible embodiment of the invention, the back-end device comprises a sleeve latch that is rotationally affixed to the chassis. The sleeve latch is arranged to engage the rotary sleeve in a locked position to prevent the rotary sleeve from rotating within the chassis. The sleeve latch is arranged to be translated in a distal direction into an unlocked position so as to disengage the rotary sleeve to allow for a rotation of the rotary sleeve within the chassis. The sleeve latch is, additionally to the release element, an additional means that needs to be released to initiate the injection cycle. Thus, the user is required to perform two separate actions to start the injection. This prevents a premature and/or inadvertent exposure of the injection needle and minimizes the risk of accidental needle stick injuries.

Preferably, the sleeve latch is biased towards the locked position by a biasing element and is retained in the unlocked position by a force exerted by the user of the auto-injector. The sleeve latch thus returns to the locked position to rotationally affixing the rotary sleeve upon removal of the force.

According to yet another possible embodiment of the invention, the release element comprises a chamfered surface that abuts against a projection of the rotary sleeve. Manual actuation of the release element exerts a torque upon the rotary sleeve to release the engagement of the plunger follower with the cam surface. As the rotary sleeve is rotationally locked to the chassis by the sleeve latch in the locked position, manual actuation of the release element is prevented until the sleeve latch disengages the rotary sleeve. Thus, the user is required to perform a sequence of actions in the proper order to start the injection cycle, namely first releasing the sleeve latch and then actuating the release element. This further reduces the likelihood of inadvertently commencing the injection cycle.

According to yet another possible embodiment of the invention, the drive means driving the plunger is substantially arranged within the hollow plunger. This arrangement saves available space within the chassis that can be used for different parts of the back-end device. Furthermore, the arrangement within the hollow plunger avoids interference of the expandable drive means with other parts of the mechanism of the back-end device, so that malfunctions may be avoided.

According to the invention, the auto-injector comprises the reusable back-end device as described herein above and the packaged syringe attached to a proximal end of the back-end device. The packaged syringe comprises a syringe barrel containing a dose of a medicament,
a stopper fluid-tightly sealing a distal end of the syringe barrel and
the injection needle in fluid communication with an interior of the syringe barrel. The plunger arranged in the proximal position abuts against the stopper and may be spaced apart from the stopper when the plunger is withdrawn from the proximal position in the distal direction. However, in some cases there may be zero distance between the stopper and the plunger when withdrawn. The initial gap between plunger and stopper allows for variable fill volume in the syringe. As soon as the plunger is released it comes into contact with the stopper, and remains in contact until the stopper has fully 'bottomed out' in the syringe at the end of the delivery of medicament. It is then withdrawn by at least the needle insertion distance, allowing the syringe to withdraw the needle from the patient, so the plunger and stopper will end up either still in contact or else separated by the amount the plunger withdrawal via the cam exceeds the needle insertion distance. This distance may be zero in some instances or combinations of back-end device and packaged syringe. The auto-injector according to the invention further combines the aforementioned advantages of the re-usable back-end device with the benefits of having a disposable packaged syringe that is inexpensive to produce. Furthermore, using a disposable packaged syringes reduces the risk of cross contamination compared to re-usable front ends, where only the syringe and needle are discarded.

According to one possible embodiment of the invention, the packaged syringe comprises a syringe retainer that is slidably arranged with respect to a transfer sleeve. The syringe retainer comprises suitable means to releasably mount the packaged syringe to the chassis of the back-end device, like for example threaded or bayonet type connection means. The slidable arrangement of the transfer sleeve and the syringe retainer allows the transfer sleeve to be axially displaced in the distal direction with respect to the chassis of the back-end device.

Preferably, the transfer sleeve is adapted to rest on the skin of a patient during the injection. Edges of the transfer sleeve may thus be rounded to avoid injuries. The transfer sleeve is arranged to abut against the sleeve latch, so that the sleeve latch is translatable from a locked position to an unlocked position by a distal translation of the transfer sleeve with respect to the syringe retainer and the chassis connected thereto. In particular, the transfer sleeve may be translated distally by pushing the auto-injector against the skin of the patient receiving the injection. The sleeve latch that is rotationally affixed to the chassis engages the rotary sleeve in the locked position to prevent the rotary sleeve from rotating within the chassis. When the transfer sleeve is pushed against the skin of the patient, the sleeve latch is translated distally into the unlocked position to disengage from the rotary sleeve to allow for a rotation of the rotary sleeve within the chassis. This in turn allows for a manual actuation of the release element so as to initiate the injection cycle. The interaction of the axially translatable transfer sleeve with the sleeve latch ensures that the auto-injector is placed properly onto the injection site before the injection is carried out.

According to another possible embodiment of the invention, a support sleeve mounts the syringe barrel with the injection needle connected to a proximal end thereof. The support sleeve is slidably arranged with respect to the transfer sleeve. The support sleeve is axially translatable with respect to the transfer sleeve by an axial translation of the plunger. The injection needle is exposed by axially translating the plunger and hence the syringe and support sleeve in the proximal direction. The injection needle only protrudes from the proximal end of the transfer sleeve during the injection and is otherwise shielded by the transfer sleeve to prevent accidental needle stick injuries.

Additionally, the support sleeve may be biased in the distal direction by a spring means to aid the withdrawal of the injection needle from the skin of the patient in the needle withdrawal phase of the injection.

According to yet another embodiment of the invention, the plunger spaced apart from the stopper is arranged to allow for a refraction of injection needle into the transfer sleeve by the action of the spring means to ensure needle safety after the dose of the medicament has been completely delivered.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
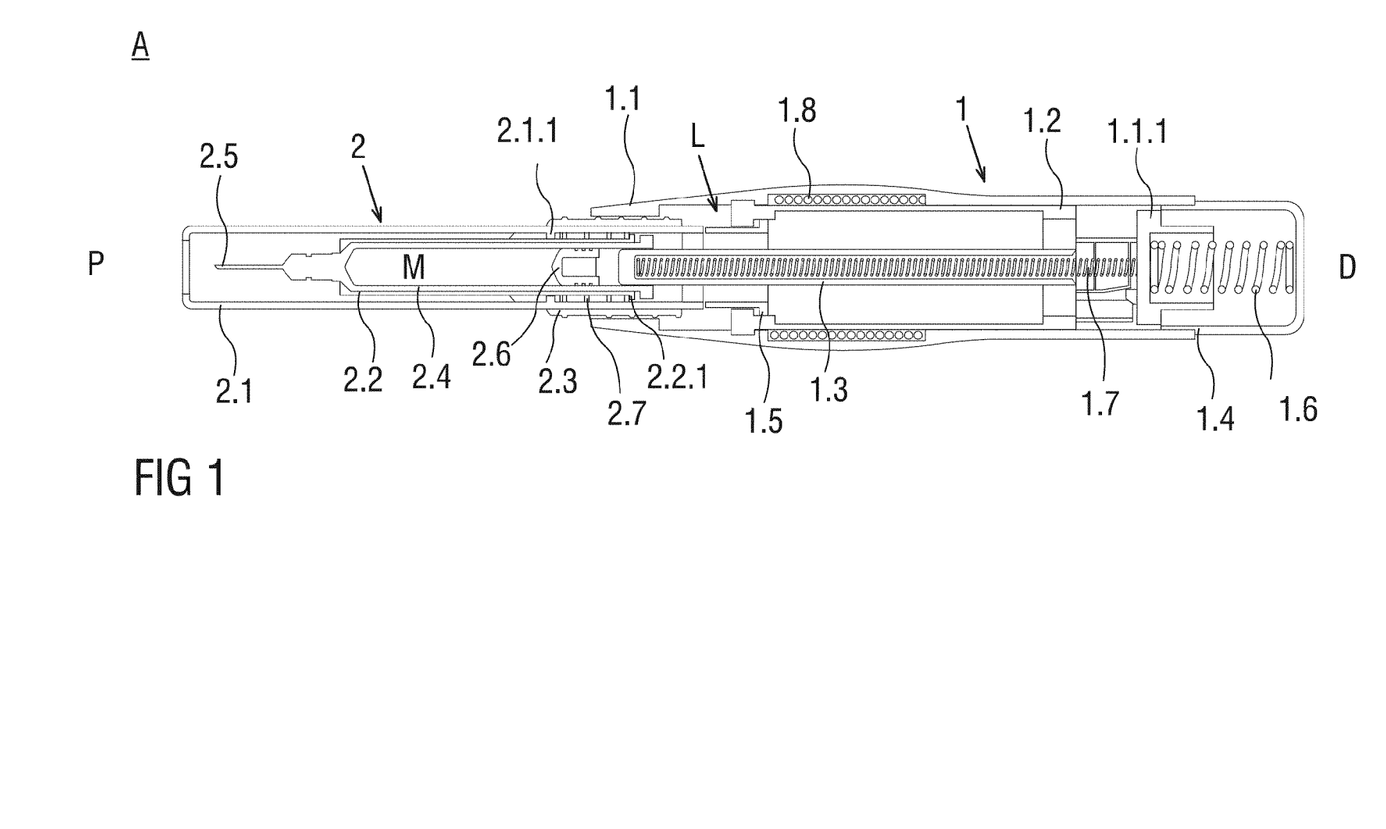
FIG. 1 shows a first sectional view of an auto-injector comprising a reusable back-end device and a packaged syringe.

FIG. 1 shows a first sectional view of an auto-injector A comprising a substantially cylindrical and reusable back-end device 1 and a packaged syringe 2 in an initial state.

The disposable packaged syringe is attached to the proximal end of the back-end device 1 and comprises a substantially tubular transfer sleeve 2.1, a support sleeve 2.2 retained within the transfer sleeve 2.1, a tubular syringe retainer 2.3 encompassing a distal section of the transfer sleeve 2.1, a syringe barrel 2.4 containing a dose of a medicament M, an injection needle 2.5 attached to a proximal end of the syringe barrel 2.4 and a stopper 2.6 providing a liquid-tight seal of a distal end of the syringe barrel 2.4.

The syringe barrel 2.4 is mounted to the support sleeve 2.2 that is axially translatably arranged with respect to the transfer sleeve 2.1. A spring means 2.7 bears against an inner rib 2.1.1 formed to an inner surface of the transfer sleeve 2.1 and against an annular collar 2.2.1 formed to a distal end of the support sleeve 2.2 to bias the support sleeve 2.2 in a distal direction 'D.

The syringe retainer 2.3 mounts the packaged syringe 2 to a chassis 1.1 of the back-end device 1. The syringe retainer 2.3 is slidably arranged on an outer surface of the transfer sleeve 2.1 and comprises mounting means, like a screw thread or a bayonet type coupling that is adapted to engage the chassis 1.1 to attach the packaged syringe 2 to the back-end device 1.

The reusable back-end device 2 of the auto-injector A comprises a rotary sleeve 1.2 retained within the chassis 1.1, a plunger 1.3 adapted to push the stopper 2.6 of the packaged syringe 2 in a proximal direction P to expel the dose of the medicament M through the injection needle 2.5, a release element 1.4 adapted to be manually actuated by a user to initiate the injection mechanism of the auto-injector A and a sleeve latch 1.5 that is rotationally affixed to the chassis 1.1 and axially translatable arranged with respect to the chassis

1.1. The sleeve latch 1.5 is initially arranged in a locked position L. In the locked position L, the sleeve latch 1.5 engages the rotary sleeve 1.2 to rotationally affix the rotary sleeve 1.2 with respect to the chassis 1.1. The sleeve latch 1.5 is translatable from the locked position L in the distal direction D to an unlocked position, in which the sleeve latch 1.5 disengages the rotary sleeve 1.5 to allow for a rotation of the rotary sleeve 1.5 with respect to the chassis 1.1. The sleeve latch 1.5 is biased by a biasing element (not illustrated) towards the locked position. The biasing element may be a spring reacting against a flange at the distal end of the sleeve latch 1.5 (not illustrated).

The transfer sleeve 2.1 is arranged to abut against the sleeve latch 1.5 as to translate the sleeve latch 1.5 in the distal direction D into the unlocked position when the transfer sleeve 2.1 is pushed against the skin of the patient receiving the injection.

According to the embodiment illustrated in FIG. 1, the release element 1.4 is arranged as a push button and mounted to a distal end of the back-end device 1. A biasing means 1.6 that is grounded to a chassis component 1.1.1 biases the release element 1.4 in the distal direction D. The release element 1.4 is fixed against rotation in the chassis 1.1 so it can apply a torque to the rotary sleeve 1.2 via a chamfered surface 1.4.1 on the release element 1.4 when activated.

A drive means 1.7 is arranged within the hollow plunger 1.3 and grounded to the chassis component 1.1.1 firmly attached to or, alternatively, integral with a distal end of the chassis 1.1. The drive means 1.7 is arranged as a compression spring and capable of, upon release, driving the plunger 2.6 in the proximal direction P to insert the injection needle 2.5 into the skin of a patient and to depress the stopper 2.6 into the syringe barrel 2.4 to dispose the dose of the medicament M beneath the skin of the patient.

A torsion spring 1.8 grounded to the chassis 1.1 exerts a torque upon the rotary sleeve 1.2. The rotary sleeve 1.2 is biased by the torsion spring to rotate within the chassis 1.1. The sleeve latch 1.5 in the locked position L prevents the rotary sleeve 1.2 from rotating within the chassis 1.1.

Figure 2:
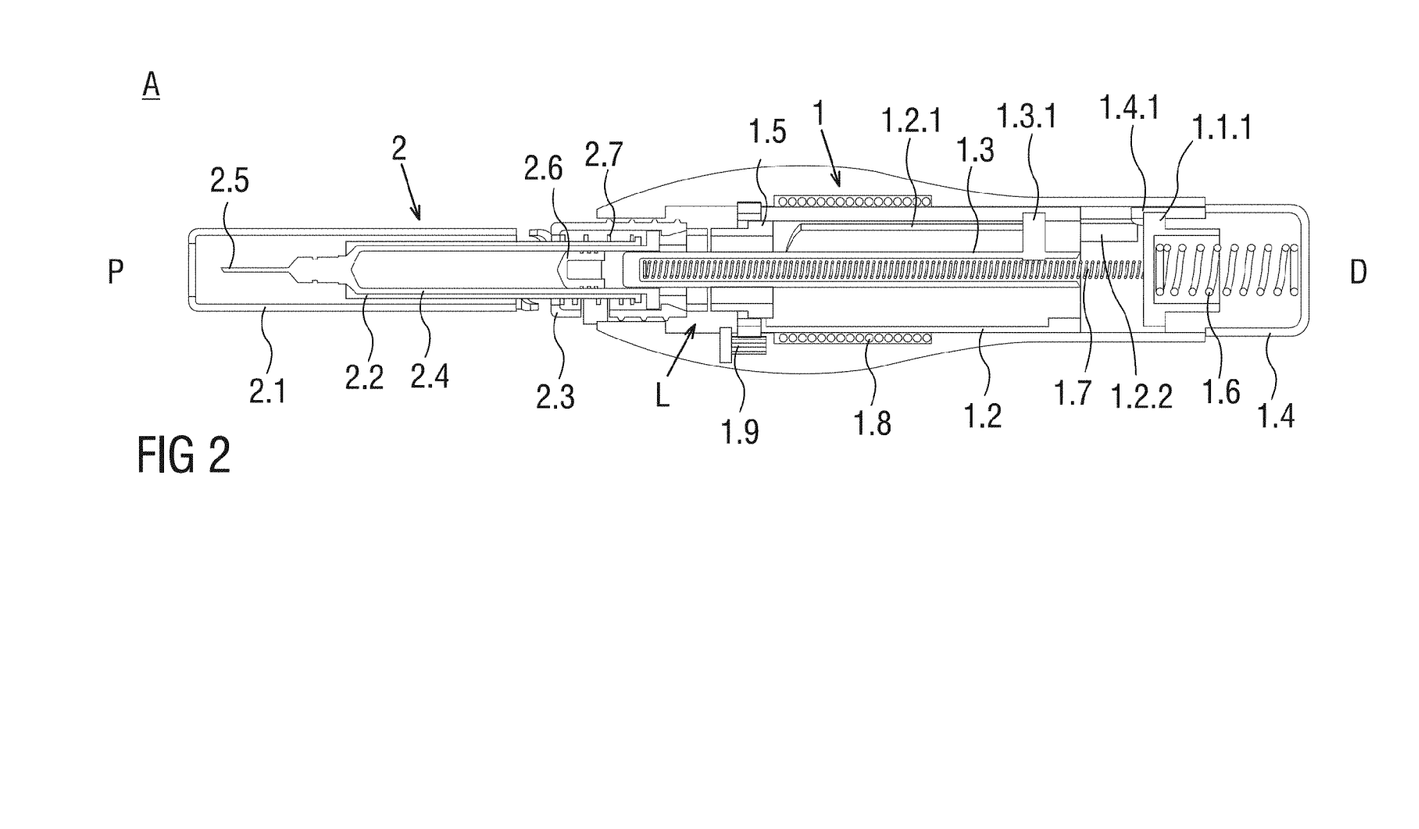
FIG. 2 shows a second sectional view of the auto-injector comprising the reusable back-end device and the packaged syringe.

FIG. 2 shows a second sectional view of the auto-injector A with the packaged syringe 2 attached to the proximal end of the back-end device 1. For illustrative purposes, the chassis 1.1 of the back-end device 1 is not shown.

A plunger follower 1.3.1 projects from the plunger 1.3 in a radial outward direction and engages a cam surface 1.2.1 formed into an inner surface of the rotary sleeve 1.2. The engagement of the plunger follower 1.3.1 and the cam surface 1.2.1 prevents an axial displacement of the plunger 1.3 that is biased in the proximal direction P by the drive means 1.7. The plunger 1.3 is splined to the chassis 1.1 so as to prevent a relative rotation of the plunger 1.3 and the chassis 1.1 (not illustrated).

The plunger follower 1.3.1 engages a distal part the cam surface 1.2.1 arranged as a latch so as to prevent an axial translation of the plunger 1.3. The cam surface 1.2.1 extends over a circumferential section of the rotary sleeve 1.2. The plunger follower 1.3.1 is arranged to disengage the distal part of the cam surface 1.2.1 upon rotation of the rotary sleeve 1.2 by a small degree with respect to the plunger 1.3.

The chamfered surface 1.4.1 on the release element 1.4 abuts on a projection 1.2.2 formed to a distal end of the rotary sleeve 1.2 and projecting therefrom in the distal direction D. The chamfered surface 1.4.1 is arranged to engage the projection 1.2.2 when the release element 1.4 is pushed proximally so as to cause the rotary sleeve 1.2 to rotate with respect to the chassis 1.1 and the plunger 1.3, whereby the plunger follower 1.3.1 disengages the cam surface 1.2.1 to allow for an axial translation of the plunger 1.3.

A rotary damper 1.9 is arranged near the proximal end of the rotary sleeve 1.2. The rotary damper 1.8 is arranged to apply a velocity dependent torque upon the rotary sleeve 1.2 so as to restrict the rotation the rotary sleeve 1.2 that rotates under the action of the torsion spring to a constant rotation velocity.

Figure 3:
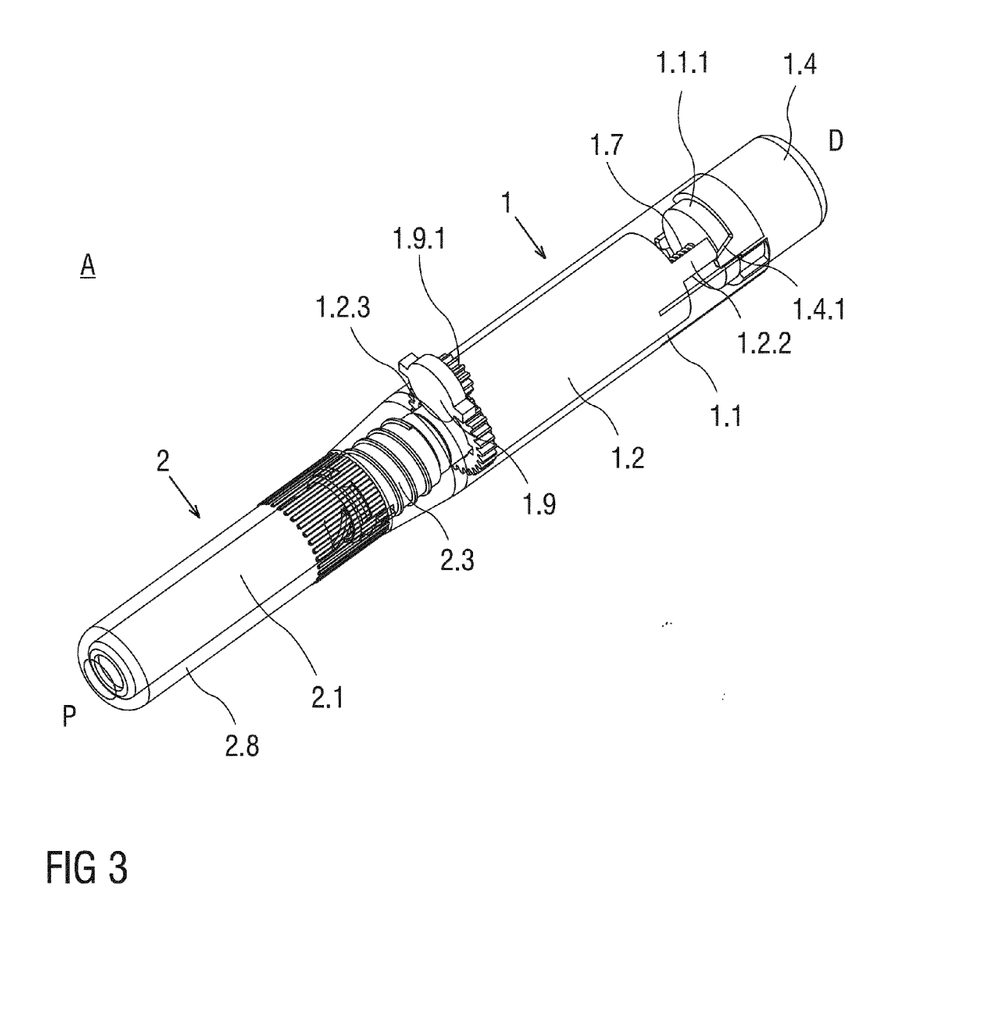
FIG. 3 shows the auto-injector in a first isometric view.

FIG. 3 shows the auto-injector A in a first isometric view. For better illustration of the inner mechanism of the auto-injector A, the chassis 1.1 and a tubular protective sheath 2.8 that covers a proximal section of the packaged syringe 2 before the injection are shown transparently.

The protective sheath 2.8 is initially screwed onto the syringe retainer 2.3 of the packaged syringe 2 to prevent accidental needle stick injuries when the packaged syringe 2 is attached to the back-end device 3. Before the injection is carried out, the protective sheath 2.8 is removed from the packaged syringe 2.

The rotary damper 1.9 comprises a first cog wheel 1.9.1 that is arranged to engage a corresponding second cog wheel 1.2.3 formed to an outer surface of the rotary sleeve 1.2. The rotary damper 1.9 viscously dampens the rotary motion of the rotary sleeve 1.2 during the injection.

If the auto-injector A was used for an injection beforehand, the back-end device 1 is reset for use before a second injection may be delivered. The back-end device 1 is reset by using a base station or appropriate tool (not illustrated). The base station or tool compresses the drive means 1.7, preloads the torsion spring 1.8, and resets the rotation of the rotary sleeve 1.2. FIGS. 1 to 3 show the back-end device 1 in the reset state.

In the reset state, the preload from the torsion spring 1.8 exerts a torque upon the rotary sleeve 1.2. Initially, the rotary sleeve 1.2 is rotationally locked by the sleeve latch 1.5 engaging the rotary sleeve 1.2 in the locked position L. Rotation of the sleeve latch 1.5 is prevented by a spline engagement of the sleeve latch 1.5 with the chassis 1.1 (not illustrated).

The plunger 1.3 is biased in the proximal direction P by the drive means 1.7. The biasing force exerted upon the plunger 1.3 is resolved through the plunger follower 1.3.1 engaging the cam surface 1.2.1 on the rotary sleeve 1.2. The plunger 1.3 is fixed in rotation by a spline feature engagement with the chassis 1.1 (not illustrated).

When the release element 1.4 is pushed to commence the injection cycle delivering the dose of the medicament M beneath the skin of the patient, the chamfered surface 1.4.1 engages the projection 1.2.2 to rotate the rotary sleeve 1.2, whereby the plunger follower 1.3 disengages the cam surface 1.2.1 to release the plunger 1.3. However, as long as the sleeve latch 1.5 rotationally locks the rotary sleeve 1.2 in the locked position, a rotation of the rotary sleeve 1.2 and hence a manual actuation of the release element 1.4 is prevented.

Before the injection, the user assembles the packaged syringe 2 to the proximal end of the reset back-end device 2 and the protective sheath 2.8 is removed from the proximal section of the packaged syringe 2. The user then places the assembled auto-injector A against the skin of the patient at the injection site so that the proximal end of the transfer sleeve 2.1 rests on the skin. As the auto-injector A is pushed against the skin, the transfer sleeve 2.1 translates in the distal direction D and displaces the sleeve latch 1.5 distally into the unlocked position.

The sleeve latch 1.5 in the unlocked position releases the rotational affixture of the rotary sleeve 1.2. The rotary constraint of the rotary sleeve 1.2 is removed and the auto-injector A is unlocked so as to allow for an actuation of the release element 1.4 initiating the injection cycle. Once the sleeve latch 1.2 reaches the unlocked position, the preload of the torsion spring 1.8 applied to the rotary sleeve 1.2 is resolved by the plunger follower 1.3.1 engaging the cam surface 1.2.1. The friction between the plunger follower 1.3.1 and the cam surface 1.2.1 on the rotary sleeve 1.2 arising from the contact force exerted upon the plunger 1.3 by the drive means 1.7 exceeds the preload of the torsion spring 1.8. Hence, the rotary sleeve 1.2 is prevented from rotating until the release element 1.4 is actuated.

The user pushes the release element 1.4 against the biasing force provided by the biasing means 1.6 in the proximal direction P to commence the injection process. As the release element 1.4 is depressed, the chamfered surface 1.4.1 on the release element 1.4 abuts against the projection 1.2.2 of the rotary sleeve 1.2. The proximal movement of the release element 1.4 applies a torque to the rotary sleeve 1.2 which is sufficient to overcome the friction between the plunger follower 1.3.1 and the cam surface 1.2.1.

The rotary sleeve 1.2 is forced to rotate by the proximal movement of the release element 1.4. The plunger follower 1.3.1 disengages the cam surface 1.2.1. This enables the plunger 1.3 to move in the proximal direction P to abut against the stopper 2.6.

The driving force exerted upon on the plunger 1.3 by the drive means 1.7 is now resolved through the stopper 2.6 retained in the syringe barrel 2.4. The resistance required to depress the stopper 2.6 into the syringe barrel 2.4 is large enough to prevent a proximal displacement of the stopper 2.6 until the support sleeve 2.2 mounting the syringe barrel 2.4 is translated in the proximal direction P against the biasing force of the spring means 2.7 and the injection needle 2.5 is inserted into the skin of the patient.

The spring means 2.7 is compressed and the injection needle 2.5 penetrates the skin of the patient. An insertion depth of the injection needle 2.5 into the skin of the patient may be controlled by a feature of the packaged syringe 2 that limits the proximal displacement of the support sleeve 2.2 with respect to the transfer sleeve 2.1 and hence limits an axial length by which the injection needle 2.5 protrudes from the transfer sleeve 2.1 in the proximal direction P. Alternatively, the injection depth may be controlled by a depth stop (not illustrated) arranged within the back-end device 1 or by full compression of the drive means 1.7.

During the needle insertion phase of the injection cycle, the cam surface 1.2.1 on the rotary sleeve 1.2 does not contact the plunger follower 1.3.1, so that the support sleeve 2.2 is translatable to insert the injection needle 2.5 by a proximal movement of the plunger 1.3.

When the injection needle 2.5 reaches the desired insertion depth, the friction opposing the motion of the stopper 2.6 within the syringe barrel 2.2 is overcome and the stopper 2.6 moves proximally to expel the dose of the medicament M through the injection needle 2.5.

Once the cam surface 1.2.1 on the rotary sleeve 1.2 is disengaged by the plunger follower 1.3.1, the rotary sleeve 1.2 starts rotating within the chassis 1.1 under the action of the torsion spring 1.8. The second cog wheel 1.2.3 integral with the rotary sleeve 1.2 engages the correspondingly shaped first cog wheel 1.9.1 of the rotary damper 1.9, which applies upon the rotary sleeve 1.2 a velocity dependent torque. As a result, the rotary sleeve 1.2 rotates at a constant speed. Appropriate selection of the rotary damper 1.9 and the torsion spring 1.8 restricts the maximal rotation speed of the rotary sleeve 1.2 to a pre-determined constant value.

Furthermore, the rotation speed determines a time delay. The cam surface 1.2.1 re-engages the plunger follower 1.3.1 after the time delay has passed.

The rotation speed of the rotary sleeve 1.2 is set to ensure total rotation of the rotary sleeve 1.2 during the injection cycle is less than one revolution, wherein the injection cycle comprises the needle insertion phase, an injection phase delivering the dose of the medicament M and a needle withdrawal phase after the dose of the medicament M has been delivered.

The plunger 1.3 continues to move proximally under the action of the drive means 1.7 until the stopper 2.6 bottoms out and reaches a proximal end of the syringe barrel 2.2 to fully empty the syringe barrel 2.2. The plunger 1.3 reaches a proximal position and the movement of the plunger 1.3 is stopped. Throughout the injection phase of the injection cycle, the plunger follower 1.3.1 does not contact the cam surface 1.2.1 on the rotary sleeve 1.2.

The time delay determined by the rotation speed of the rotary sleeve 1.2 is longer than the time span required for the plunger 1.3 to fully depress into the syringe barrel 2.4. Hence, the time delay is adapted to allow for a complete expelling of the dose of the medicament M before the cam surface 1.2.1 re-engages the plunger follower 1.3.1.

During the injection phase, the rotary sleeve 1.2 continues to rotate at constant speed under the action of the torsion spring 1.8 resolved through the rotary damper 1.9. Shortly after the stopper 2.6 bottoms out in the syringe barrel 2.4, the rotary sleeve 1.2 further rotates with respect to the plunger 1.3 and the chassis 1.1, the cam surface 1.2.1 regains contact with the plunger follower 1.3.1. The torsion spring 1.8 and the viscous dampening of the rotary damper 1.9 are adapted to ensure that the rotational speed of the rotary sleeve 1.2 is sufficiently slow, so that the stopper 2.6 has bottomed out and the dose of the medicament M is fully delivered before the plunger follower 1.3.1 regains contact with the cam surface 1.2.1.

The geometry of a proximal part of the cam surface 1.2.1 on the rotary sleeve 1.2 comprises a ramp that is configured to abut against the plunger follower 1.3.1. The rotary sleeve 1.2 continues to rotate after the injection phase is completed, whereby the cam surface 1.2.1 abuts the plunger follower 1.3.1 to withdraw the plunger 1.3 away from the stopper 2.6 in the distal direction D. The axial displacement of the plunger 1.3 in the distal direction D during withdrawal is at least as great as a needle insertion distance which is the distance travelled by the plunger 1.3 during needle insertion. This allows the spring means 2.7 of the packaged syringe 2 to drive the support sleeve 2.2 mounting the syringe barrel 2.4 back in the distal direction D to withdraw the injection needle 2.5 from the injection site. With the injection needle 2.5 retracted from the skin of the patient, the needle withdrawal phase and thus the last phase of the injection cycle is completed.

The user may now remove the emptied packaged syringe 2 from the reusable back-end device 1 and reset the back-end device 1 using the tool or the base-station as described herein above to prepare the back-end device 1 for a subsequent injection.

The invention claimed is:

1. A back-end device of an auto-injector adapted to be attached to a packaged syringe, the back-end device comprising:
   a chassis,
   a plunger arranged to abut against a stopper of the packaged syringe to translate an injection needle of the packaged syringe in a proximal direction and to expel a dose of a medicament contained in the packaged syringe through the injection needle, a drive spring capable of, upon release, driving the plunger in the proximal direction towards a proximal position, a rotary sleeve with a cam surface adapted to be engaged by a plunger follower formed to the plunger, a torsion spring arranged to exert a torque upon the rotary sleeve, the torsion spring being configured to bias the rotary sleeve to rotate, and a release element comprising a push button, the release element being capable of, upon manual actuation, releasing the engagement of the plunger follower with the cam surface, wherein the plunger follower is arranged to engage the cam surface to inhibit the rotary sleeve from rotating with respect to the chassis and to inhibit an axial translation of the plunger in the proximal direction in an initial state, wherein, upon release of the engagement of the plunger follower with the cam surface, the rotary sleeve is arranged to rotate within the chassis so that the cam surface re-engages the plunger follower after a time delay determined by a rotation speed of the rotary sleeve, the time delay being set to allow the cam surface to re-engage the plunger follower after the plunger reaches the proximal position, and wherein the cam surface is arranged to withdraw the plunger from the proximal position in a distal direction by continued rotation of the rotary sleeve.

2. The back-end device according to claim 1, further comprising a rotary damper arranged to exert a velocity dependent torque upon the rotary sleeve to restrict a maximal rotation speed of the rotary sleeve.

3. The back-end device according to claim 2, wherein the rotary damper comprises a first cog wheel configured to engage a second cog wheel of the rotary sleeve.

4. The back-end device according to claim 1, further comprising a sleeve latch rotationally affixed to the chassis, wherein the sleeve latch arranged to engage the rotary sleeve to inhibit the rotary sleeve from rotating within the chassis when the sleeve latch is in a locked position, and wherein the sleeve latch is arranged to be translated in the distal direction into an unlocked position such that the sleeve latch disengages from the rotary sleeve to allow for a rotation of the rotary sleeve within the chassis when the sleeve latch is in the unlocked position.

5. The back-end device according to claim 4, wherein the sleeve latch is biased towards the locked position by a biasing element.

6. The back-end device according to claim 1, wherein the release element comprises a chamfered surface configured to abut against a projection of the rotary sleeve so that, upon manual actuation, the release element exerts a torque upon the rotary sleeve to release the engagement of the plunger follower with the cam surface.

7. The back-end device according to claim 1, wherein the plunger is hollow, and the drive spring is substantially arranged within the plunger.

8. The back-end device according to claim 1, wherein a modulus of resilience of the drive spring and a modulus of resilience of the torsion spring are selected such that the time delay allows the cam surface to re-engage the plunger follower after the plunger reaches the proximal position.

9. The back-end device according to claim 1, wherein a distal portion of the cam surface defines a latch configured to inhibit the axial translation of the plunger, and the plunger follower is configured to disengage from the latch when the rotary sleeve is rotated relative to the plunger.

10. The back-end device according to claim 1, wherein the plunger follower and the cam surface are configured such that a friction force between the plunger follower and the cam surface exceeds a preload of the torsion spring to inhibit the axial translation of the plunger in the proximal direction in the initial state.

11. An auto-injector comprising:

a reusable back-end device and a packaged syringe attached to a proximal end of the back-end device, wherein the packaged syringe comprises a syringe barrel containing a dose of a medicament, a stopper fluid-tightly sealing a distal end of the syringe barrel, and an injection needle in fluid communication with an interior of the syringe barrel, wherein the reusable back-end device comprises a chassis, a plunger arranged to abut against the stopper of the packaged syringe to translate the injection needle of the packaged syringe in a proximal direction and to expel the dose of the medicament contained in the packaged syringe through the injection needle, a drive spring capable of, upon release, driving the plunger in the proximal direction towards a proximal position, a rotary sleeve with a cam surface adapted to be engaged by a plunger follower formed to the plunger, a torsion spring arranged to exert a torque upon the rotary sleeve, the torsion spring being configured to bias the rotary sleeve to rotate, and a release element comprising a push button, the release element being capable of, upon manual actuation, releasing the engagement of the plunger follower with the cam surface, wherein the plunger follower is arranged to engage the cam surface to inhibit the rotary sleeve from rotating with respect to the chassis and to inhibit an axial translation of the plunger in the proximal direction in an initial state, wherein, upon release of the engagement of the plunger follower with the cam surface, the rotary sleeve is arranged to rotate within the chassis so that the cam surface re-engages the plunger follower after a time delay determined by a rotation speed of the rotary sleeve, the time delay being set to allow the cam surface to re-engage the plunger follower after the plunger reaches the proximal position, wherein the cam surface is arranged to withdraw the plunger from the proximal position in a distal direction by continued rotation of the rotary sleeve, and wherein the plunger in the proximal position abuts against the stopper and is arranged to be withdrawn from the proximal position in the distal direction.

12. The auto-injector according to claim 11, further comprising a syringe retainer slidably arranged with respect to a transfer sleeve, the transfer sleeve being configured to releasably mount the packaged syringe to the chassis of the back-end device.

13. The auto-injector according to claim 12, further comprising a sleeve latch rotationally affixed to the chassis, wherein the transfer sleeve is adapted to rest on skin of a patient during an injection, the transfer sleeve being configured to abut against the sleeve latch so that the sleeve latch is translatable from a locked position to an unlocked position by a distal translation of the transfer sleeve with respect to the syringe retainer, and wherein the sleeve latch is rotationally affixed to the chassis and is configured to engage the rotary sleeve to inhibit the rotary sleeve from rotating within the chassis when the sleeve latch is in the locked position, and the sleeve latch is configured to disengage from the rotary sleeve to allow for a rotation of the rotary sleeve within the chassis when the sleeve latch is in the unlocked position.

14. The auto-injector according to claim 12, further comprising a support sleeve to which the syringe barrel is mounted, wherein the support sleeve is slidably arranged with respect to the transfer sleeve and is axially translatable with respect to the transfer sleeve by an axial translation of the plunger.

15. The auto-injector according to claim 14, wherein the support sleeve is biased in the distal direction by a spring.

16. The auto-injector according to claim 15, wherein the plunger is arranged to allow for a retraction of the injection needle into the transfer sleeve by action of the spring when the plunger is spaced apart from the stopper.

17. The auto-injector according to claim 11, further comprising a rotary damper arranged to exert a velocity dependent torque upon the rotary sleeve to restrict a maximal rotation speed of the rotary sleeve.

18. The auto-injector according to claim 11, wherein a modulus of resilience of the drive spring and a modulus of resilience of the torsion spring are selected such that the time delay allows the cam surface to re-engage the plunger follower after the plunger reaches the proximal position.

19. The auto-injector according to claim 11, wherein a distal portion of the cam surface defines a latch configured to inhibit the axial translation of the plunger, and the plunger follower is configured to disengage from the latch when the rotary sleeve is rotated relative to the plunger.

20. The auto-injector according to claim 11, wherein the plunger follower and the cam surface are configured such that a friction force between the plunger follower and the cam surface exceeds a preload of the torsion spring to inhibit the axial translation of the plunger in the proximal direction in the initial state.

* * * * *